United States Patent

Soula et al.

[11] Patent Number: 5,780,579
[45] Date of Patent: Jul. 14, 1998

[54] METHOD FOR THE PREPARATION OF POLYAMINO ACIDS

[75] Inventors: Gérard Soula, Meyzieu; Jean-Michel Grosselin; Rafaël Jorda, both of Ste Foy Les Lyon; Catherine Castan, Brignais, all of France

[73] Assignee: Flamel Technologies (Societe Anonyme), Venissieux Cedex, France

[21] Appl. No.: 592,299

[22] PCT Filed: Aug. 9, 1994

[86] PCT No.: PCT/FR94/00992

§ 371 Date: Mar. 28, 1996

§ 102(e) Date: Mar. 28, 1996

[87] PCT Pub. No.: WO95/04772

PCT Pub. Date: Feb. 16, 1995

[30] Foreign Application Priority Data

Aug. 10, 1993 [FR] France ................................. 93 09991

[51] Int. Cl.⁶ .............................................. C08G 69/26
[52] U.S. Cl. .......................... 528/332; 528/310; 528/315; 528/317; 530/333; 530/338
[58] Field of Search .............................. 528/332, 310, 528/315, 317; 530/333, 388

[56] References Cited

U.S. PATENT DOCUMENTS 3,536,672  10/1970  Fujimoto et al. .

FOREIGN PATENT DOCUMENTS

A-996 760     6/1965   United Kingdom .
A-1 024 393   3/1966   United Kingdom .
A-1 202 765   8/1970   United Kingdom .

*Primary Examiner*—Duc Truong
*Attorney, Agent, or Firm*—Bacon & Thomas

[57] ABSTRACT

The present invention relates to a method for the preparation of polyamino acids, with controlled molecular weights, by polymerization of N-carboxyanhydrides (NCAs) of at least one amino acid, using at least one initiator of the strong base type and in liquid medium, characterized in that it consists in including, in the liquid reaction medium, given amounts of water and/or of alcohol. Application: synthesis of polyamino acids with mechanical and rheological characteristics adapted to applications as biomaterials.

16 Claims, 2 Drawing Sheets

METHOD FOR THE PREPARATION OF POLYAMINO ACIDS

This application is a 371 PCT/FR 94/00992 filed Aug. 9, 1994.

TECHNICAL FIELD

The present invention belongs in the technical field of the synthesis of polyamino acids from amino acid N-carboxyanhydrides (referred to hereinbelow as NCAs).

Even more precisely, the present invention relates to the polymerization, in liquid medium, of NCAs by polymerization initiators of strong base type.

PRIOR ART

Polyamino acids are biocompatible and biodegradable polymers which find applications in the biomedical field. In particular, they may constitute biomaterials which are useful, for example, as starting materials for the manufacture of prostheses and implants or alternatively for use as supports which allow the release of active principles. Applications of polyamino acids as resorbable suture threads, as temporary skin substitutes or as textile fibers have also been described.

In order to be usable in these various applications, it is important for it to be possible for the polyamino acids to be in a liquid or semi-liquid form, which can be handled in the context of operations for forming finished articles, such as the formation of films, spinning, molding, etc. This therefore implies control of the intrinsic viscosity and/or of the weight-average molar mass $M_w$ of the polyamino acid synthesized.

In addition and in contrast to this, it is desirable for these polyamino acids to have a molar mass $M_w$ greater than a threshold which may be set, for example, at $M_w$=50,000, below which they do not satisfy the structural and mechanical properties expected in the applications envisaged.

The book by H. R. Kricheldorf, "α-amino acid-N-carboxyanhydrides and related heterocycles", Springer-Verlag (1987), teaches that the polymerization of NCAs is generally carried out in liquid medium, using polymerization initiators which may be protic nucleophiles, such as water, primary amines and secondary amines, or strong bases, such as alkoxides or tertiary amines or phosphines. Besides these strong bases, English [sic] patent GB-996,760 proposes organometallic reagents such as trialkyllithiums or trialkylaluminums as NCA polymerization initiators.

Kricheldorf specifies (page 92) that the polymerization of NCAs, initiated by protic nucleophiles, does not give rise to high molecular weights (DPn less than 200), in contrast with initiators of the strong base type which give access to polymers of DPn greater than 200. Since these polymers are precisely those which prove to be suitable for the applications of the polyamino acids, initiation of the polymerization of NCAs by strong bases has thus been the synthetic route adopted by those skilled in the art.

However, the drawback of polymerization initiators of this type is precisely that they promote the reaction so well that neither the degree of polymerization nor the molar mass $M_w$ is any longer controlled. This thus results in extremely high reduced viscosities for the polyamino acids. This is obviously disadvantageous with regard to operations for the conversion of these polymers into manufactured products.

Consequently, one of the essential aims of the present invention is to provide a method for the synthesis of polyamino acids from NCA, in liquid medium and in the presence of initiators of strong base type:

which makes it possible to obtain finished products of weight-average molar mass $M_w$ which is controllable and, advantageously, but in a nonlimiting manner, high, i.e. preferably greater than or equal to 50,000 and, even more preferably, to 80,000, which offers the possibility of controlling the reduced viscosity of these finished products and, even better, which makes it possible to target a given reduced viscosity beforehand, and, lastly, which is simple and economical to carry out.

Thus, after considerable research and experimentation, the Applicant has, to its credit, been able to demonstrate that in order to achieve this aim, inter alia, the polymerization of the NCAs should, against all expectation, be carried out in a liquid reaction medium comprising, in particular, water and/or an alcohol.

As regards the control of the molecular mass of the polyamino acids obtained, the results thus obtained are extremely surprising. The reason for this is that it was hitherto entirely accepted in the state of the art that as long as reactants such as water and alcohols are present in significant amounts, they induce a hydrolysis or alcoholysis of the NCAs and, consequently, lead to oligomers or polymers of low molecular mass: $DP_R$ of less than 200, e.g. (cf. Kricheldorf p. 60 and Becker et al., J.A.C.S., 5 Jan. 1953, pp. 737 to 744).

In addition, GB patent 996,760 teaches that the use of infinitesimal amounts of water, $10^{-2}$% by weight relative to the solvent, causes an increase in the reduced viscosity of the final polymer: 3.5 to 4.32 (Examples 1–2).

DESCRIPTION OF THE INVENTION

Despite the above, the present invention relates to a method for the preparation of polyamino acids, with controlled molecular weights, by polymerization of N-carboxyanhydrides (NCAs) of at least one amino acid, using at least one initiator of the strong base type and in liquid medium, characterized in that it consists in including, in the liquid reaction medium, given amounts of water and/or of alcohol.

By this arrangement, it is possible to control the reduced viscosity of the polymers and, consequently, their weight-average molar mass ($M_w$).

As regards the alcohol, it is preferably selected from linear or cyclic $C_{1-24}$ monoalcohols and/or dialcohols, or from aromatic alcohols and, more preferably, from the following list: methanol, ethanol, propanol, butanol, hexanol, phenols, glycols, these compounds being used alone or as a mixture with each other.

The alcohol used as a means of adjusting the reduced viscosity, and thus the molecular mass, of the finished polymer may be employed at a proportion of from 0 to 3000 mol %, preferably of from 10 to 1000 mol % and, even more preferably, of from 10 to 500 mol % relative to the NCAs.

As regards the water, it may be employed at a proportion of from 0.1 to 50% by weight relative to the rest of the liquid medium, preferably at a proportion of from 0.5 to 10% by weight and, even more preferably, of from 1 to 5% by weight.

A subsidiary advantage associated with the use of water and/or alcohol is the acceleration of the rate of polymerization.

According to an advantageous mode of the invention, the liquid medium comprises an organic cosolvent.

Thus, it is possible, in accordance with the invention, to establish, for one or more NCA monomers corresponding to different amino acids, a curve of variation of the reduced viscosity of the polymer or of the copolymer as a function of the concentration of water and/or alcohol in the reaction medium. Advantageously, this curve may be used in order to determine the amount of water and/or alcohol to be introduced into the reaction medium in order to obtain a polymer or copolymer of given viscosity. This makes it possible to make the physical characteristics of the starting material, which the polyamino acids constitute, suitable for the various shaping and conversion operations appropriate for a determined final application (thread, film, matrix, etc.).

Moreover, it should be pointed out that the use of coreactants, such as the water and/or the alcohol, is synonymous with economy and convenience of use.

The starting materials for the method according to the invention are N-carboxyanhydrides of amino acids of L, D or racemic L+D configuration. Such a starting material may be a mixture of various enantiomers and/or racemates. It is possible to use monomers of only one type consisting of an NCA of a given amino acid, or alternatively different monomers consisting of NCAs of distinct amino acids, so as to form a copolymer.

The amino acid NCAs may be prepared by any known and suitable technique such as, for example, that described by W. H. Daly et al., Tetrahedron Letters, Vol. 29, No. 6, p 5859, (1988).

The precursors of these NCAs may be chosen from the following amino acids, alone or as a mixture: from glycine, alanine, phenylalanine, leucine, isoleucine, valine, α-aminoisobutyric acid, aspartic acid, glutamic acid, α-aminoadipic acid, ornithine, lysine, arginine, cysteine, methionine, threonine, serine, tyrosine.

The concentration of the NCA monomer in the reaction medium is advantageously between 1 and 40% by weight relative to the organic solvent and preferably between 2 and 20% by weight and, even more preferably, between 4 and 15% by weight.

According to an advantageous arrangement of the invention, the initiator is chosen from tertiary amines and/or phosphines.

Among the polymerization initiators characteristic of the invention, mention may be made, for example, of triethylamine, trimethylamine, tris-N-propylamine, triisopropylamine, tributylamine, tricyclohexylamine, 4,4', 4"-tris(dimethylamino)triphenylmethane and tertiary phosphines: triphenylphosphine, trimethylphosphine, dimethylphenylphosphine, tributylphosphine, triisopropylphosphine, tricyclohexylphosphine and diphenylmethylphosphine.

In accordance with a preferred arrangement of the invention, triethylamine is used as initiator.

In terms of weight, the initiator represents a molar amount of between 0.001 and 1 molar, preferably of between 0.005 and 0.1 molar, relative to the NCA.

According to the invention, the polymerization is performed in liquid medium, which means, in other words, that it may be performed in solution or in suspension. In the case of a solution polymerization, the organic cosolvent(s) used is (are) chosen from the following chemical classes: cyclic or linear ethers, nitriles, halogenated aliphatics, aromatics, halogenated aromatics, nitro derivatives, esters, ketones, amides, sulfones, sulfoxides, or mixtures thereof.

For a suspension polymerization, the organic cosolvent is chosen from alkanes: pentane, hexane, octane or decane, for example, and fluoroalkanes, or mixtures thereof.

Halogenated aliphatic hydrocarbons which may be mentioned, for example, are chloroform, dichloromethane, 1,2-dichloromethane |sic|, 1,1-dichloroethane, 1,2-dichloroethylene, 1,1,1-trichloroethane, 1,1,2-trichloroethane, trichloroethylene, tetrachloroethylene, 1,1,2,2-tetrachloroethane, 1,1,1,2-tetrachloroethane, pentachloroethane, 1,2-dichloropropane, 2,2-dichloropropane, 1,3-dichloropropane, 1,2,3-dichloropropane, dichloroomethane |sic|, 1-bromo-3-chloropropane, isobutylene bromide and bromoform.

The cyclic ethers may be e.g. dioxane or tetrahydrofuran.

Acetonitrile is an example of a nitrile, toluene and xylene are examples of aromatics, nitromethane is an example of a nitro derivative and methyl acetate is an example of an ester.

Dimethylformamide (DMF) and dimethyl sulfoxide (DMSO) are respectively examples of an amide and of a sulfoxide which may be used. An example of a sulfone which may be mentioned is sulfolane.

It should be noted that dioxane is among the particularly preferred organic solvents.

In practice, this polymerization reaction takes place at normal atmospheric pressure, in ambient atmosphere and with a reaction medium temperature of between $-20°$ C. and $+150°$ C., preferably of between $+10°$ and $+90°$ C.

This method gives access to polyamino acids (polymers, copolymers) whose molar masses and reduced viscosity are controllable. This control is achieved without it hampering the ease of use or the economy of the method.

POSSIBILITY OF INDUSTRIAL APPLICATION

Synthesis of polyamino acids with mechanical and rheological characteristics adapted to applications as biomaterials.

The invention will be better understood and its advantages and implementation variants will emerge clearly from the examples, which follow, of illustration of the polymerization of amino acid NCAs derived from methyl glutamate and/or from leucine.

The attached figures will facilitate the understanding of the examples.

BEST WAYS OF PERFORMING THE INVENTION

EXAMPLES

Figure 1:
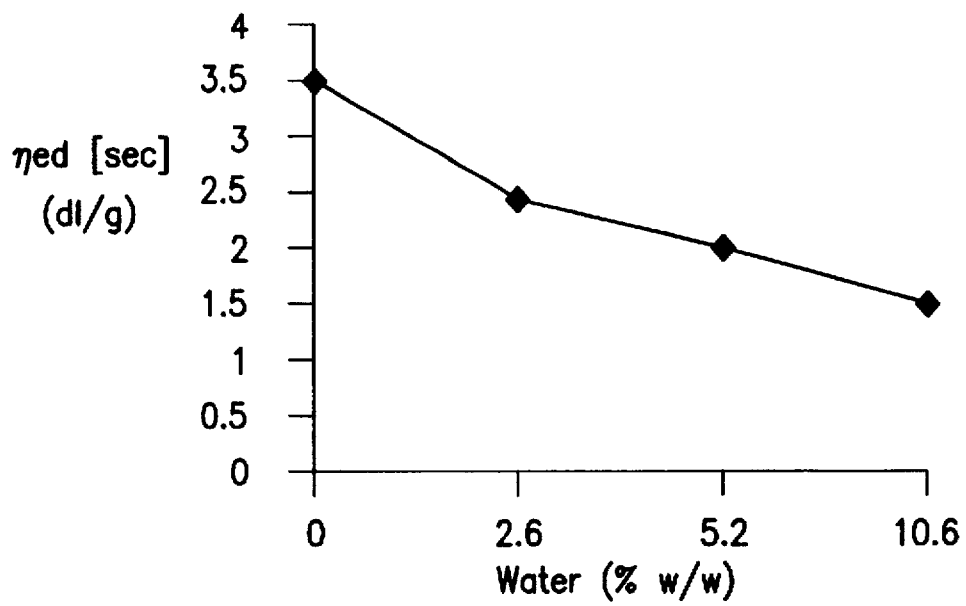
FIG. 1 shows the variation in reduced viscosity of the polymer as a function of the water added to the polymerization medium.

The reduced viscosity, which is a standard method of characterization of polyamino acids, is measured with a solution in trifluoroacetic acid (TFA) at a concentration C of 0.5 g/l. An Ubbelohde tube, ref. 510 03/0c, is used, placed in a bath thermostatically regulated to 25° C. If $t_0$ is the run-out time for pure TFA and t is the run-out time for the polymer solution, the reduced viscosity is expressed in the following way:

$$\eta_{red} = \frac{(t - t_0)}{(t \times C)}$$

The reduced viscosity reflects the weight-average molar mass $M_w$ of the polyamino acids, as shown in Example 4 below.

EXAMPLE 1

1.1 Preparation of Glu(OMe)-NCA=Methyl Glutamate N-carboxyanhydride 32.5 g of methyl glutamate and 250 ml of tetrahydrofuran (THF) are loaded into a 0.5 l reactor fitted with a condenser, a dropping funnel and a magnetic stirrer. A solution of bis-trichloromethyl carbonate (25 g) in 38 ml of THF is introduced into the dropping funnel. The reactor is placed in an oil bath at a temperature of 52° C. and placed under a stream of nitrogen. As soon as the temperature of the reaction mass reaches 50° C., addition of the triphosgene solution is commenced. The solution is run in over 20 min. The reaction medium is stirred a further 25 min and then filtered to move the insoluble materials. The filtrate is concentrated, 300 ml of cyclohexane are then added and the mixture is cooled for 15 h at −28° C. The white precipitate is filtered off. 30.7 g of crude methyl glutamate NCA are obtained. The product is recrystallized from a dichloromethane/cyclohexane mixture to give 28 g of pure methyl glutamate NCA.

Melting point=96.7° C.; heat of fusion=138.9 j/g; chloride content=0.16%.

1.2 Polymerization of Glu(OMe)-NCA 5 g of Glu(OMe)-NCA and dioxane freshly distilled over sodium (75 ml) are introduced into a 250 ml reactor flushed beforehand with nitrogen. The polymerization reactor is placed in an oil bath maintained at 40° C. and the reaction medium is stirred at 65 rev/min (the temperature of the reaction medium is 38° C.). After 10 min, 0.029 g of triethylamine is added. After reaction for 20 h, the viscous mixture is diluted with 75 ml of dioxane. The poly-Glu (OMe) is isolated by precipitation in 2 l of demineralized water at room temperature and washed twice with 500 ml of water, before being dried, in the presence of phosphorus pentoxide under water vacuum, to constant weight. 3.63 g of Glu(OMe) polymer are obtained, i.e. a yield of 95%. The reduced viscosity of the copolymer, measured in trifluoroacetic acid, is 3.54 dl/g.

1.3 Influence of Water on the Viscosity of Polymethyl Glutamate

The amount of water present in the reaction medium was studied in the 2%–10% range of water relative to the dioxane (weight ratio). Table 1 summarizes the characteristics of the polymers obtained by adding increasing amounts of water to the reaction medium.

TABLE 1

INFLUENCE OF THE AMOUNT OF WATER ON THE CHARACTERISTICS OF POLY-GLU(OMe)

| WATER/DIOXANE (weight %) | YIELD (%) | $\eta_{red}$ (dl/g) |
|---|---|---|
| 2.6 | >93 | 2.42 |
| 5.1 | >93 | 1.95 |
| 10.4 | >93 | 1.48 |

FIG. 1 attached shows the variation in reduced viscosity of the polymer as a function of the water added to the polymerization medium.

Figure 2:
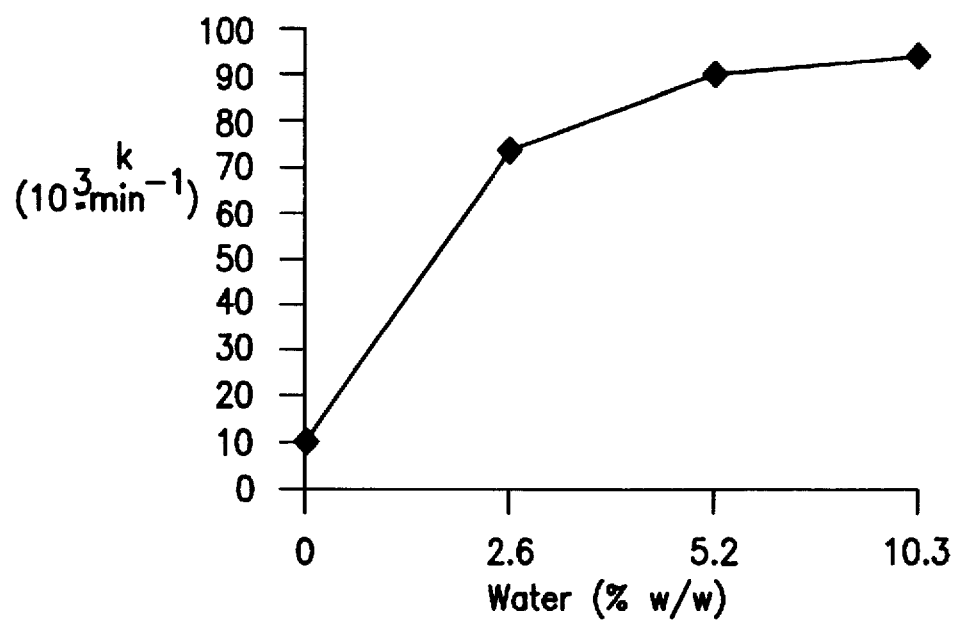
FIG. 2 represents a variation of the rate constant k for the polymerization reaction, as a function of the amount of water in the reaction medium, in the polymerization according to Example 1.

FIG. 2 attached represents the variation of the rate constant k for the polymerization reaction as a function of the amount of water in the reaction medium. This provides evidence of the beneficial effect of water on the kinetics for the polymerization of Glu(OMe)-NCA.

EXAMPLE 2

2.1 Preparation of Leu-NCA 26.5 g of leucine and 250 ml of tetrahydrofuran (THF) are loaded into a 0.5 l reactor fitted with a condenser, a dropping funnel and a magnetic stirrer. A solution of 25 g of bis-trichloromethyl carbonate (triphosgene) in 38 ml of THF is introduced into the dropping funnel. The reactor is placed in a oil bath at a temperature of 52° C. and placed under a stream of nitrogen. As soon as the temperature of the reaction mass reaches 50° C., addition of the triphosgene solution is commenced. The solution is run in over 15 min. The reaction medium is stirred for a further 30 min and is then filtered in order to remove the insoluble materials. The filtrate is concentrated, 300 ml of cyclohexane are added and the mixture is cooled for 15 h at −28° C. The white precipitate is filtered off. 24.5 g of crude leucine NCA are obtained. The product is recrystallized from a chloroform/cyclohexane mixture to give 20 g of pure Leu-NCA. Melting point=76.9° C.; heat of fusion=99.8 j/g; chloride content= 0.12%.

2.2 Polymerization of the Glu(OMe)-NCA/Leu-NCA Mixture

The Glu(OMe)-NCA and Leu-NCA mixture (5 g of 47 mol % Leu-NCA) and distilled dioxane (75 ml) are successively introduced into a 250 ml reactor, flushed beforehand with nitrogen. The polymerization reactor is placed in an oil bath maintained at 40° C. and the reaction medium is stirred at 65 rev/min (the temperature of the reaction medium is 38° C.). After 10 min, the triethylamine (0.029 g) is added rapidly. After reaction for 5 h, the viscous mixture is diluted with 75 ml of dioxane and the stirring is increased to 150 rev/min, so as to solubilize the polymer rapidly. The Leu/Glu(OMe) copolymer is isolated by precipitation in 2 l of demineralized water at room temperature and washed twice with 500 ml of water, before being dried under vacuum in the presence of phosphorus pentoxide. 3.53 g of Leu/Glu (OMe) copolymer are thus obtained, i.e. a yield of 95%. The reduced viscosity of the copolymer, measured in trifluoroacetic acid, is 3.7 dl/g.

2.3 Influence of Water on the Viscosity of the Leu/Glu(OMe) Copolymer

The amount of water present in the reaction medium was studied between 0.1% and 10% by weight relative to the dioxane. Table 2 summarizes the characteristics of the copolymer by adding increasing amounts of water to the reaction medium.

TABLE 2

INFLUENCE OF THE AMOUNT OF WATER ON THE CHARACTERISTICS OF THE Leu/Glu(OMe)

| WATER/DIOXANE (weight %) | YIELD (%) | COMPOSITION (% Leu) | $\eta_{red}$ (dl/g) |
|---|---|---|---|
| 0.1 | >93 | 47 | 3.62 |
| 1 | >93 | 49 | 3.08 |
| 5 | >93 | 48 | 1.94 |
| 10 | >93 | 47 | 1.56 |

Figure 3:
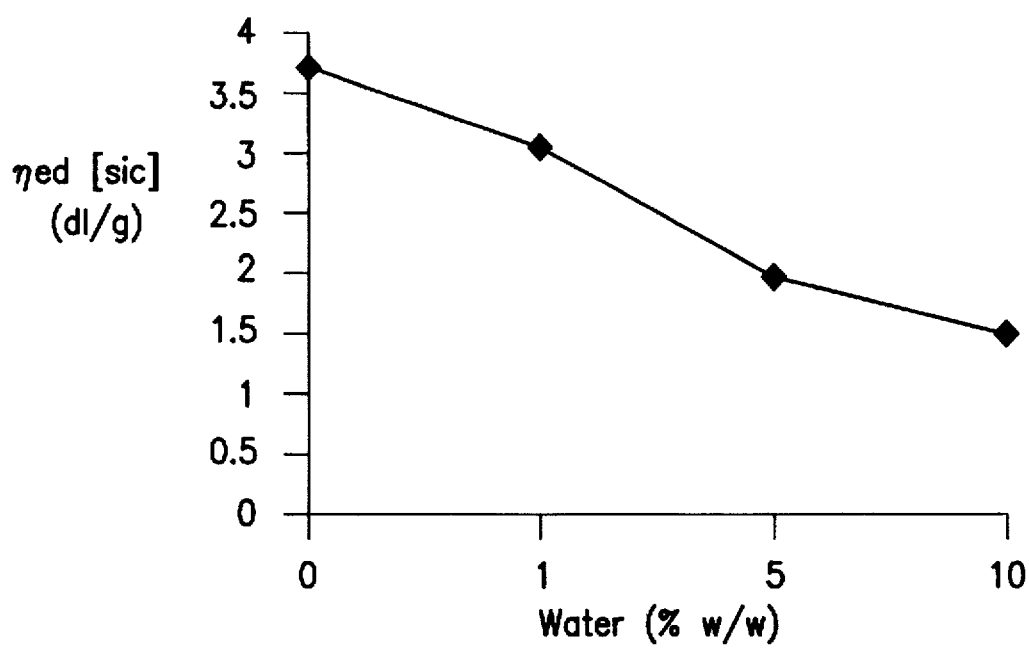
FIG. 3 illustrates the decrease in viscosity of the copolymer as a function of the amount of water added to the reaction medium.

FIG. 3 attached illustrates the decrease in viscosity of the copolymer as a function of the amount of water added to the reaction medium.

2.4 Influence of Alcohol on the Reduced Viscosity (Molecular Mass) of the Leu/Glu(OMe) Polymer The aim of this series of copolymers, composed of four products, is to vary the reduced viscosity of the copolymers and to keep their composition constant. The monomer proportions adopted are 53% of GluOMe and 47% of leucine.

The polar solvent used is absolute ethanol.

The amount of absolute ethanol was varied between 21 and 458 mol % relative to the NCAs (i.e. 0.5 and 8.5% by weight/dioxane); the proportions of monomers introduced remained constant.

The results are given in Table 3 below.

TABLE 3

| Absolute EtOH/NCA (mol %) | EtOH/dioxane (weight %) | Yield (%) | $\eta_{red}$ (dl/g) |
|---|---|---|---|
| 458 | 8.5 | 92 | 1.75 |
| 275 | 4.9 | 94 | 2.1 |
| 92 | 1.6 | 93 | 2.5 |
| 31 | 0.5 | 92 | 3.1 |

EXPERIMENTAL CONDITIONS mol % Leu/Glu(OMe)=47/53,
[Leu+Glu(OMe)] NCA=20 g (0.1123 mol),
Dioxane+absolute EtOH=300 ml,
Et$_3$N=0.125 g (1 mol %/NCA),
T=40° C.,
stirring=80 revolutions/minute.

Figure 4:
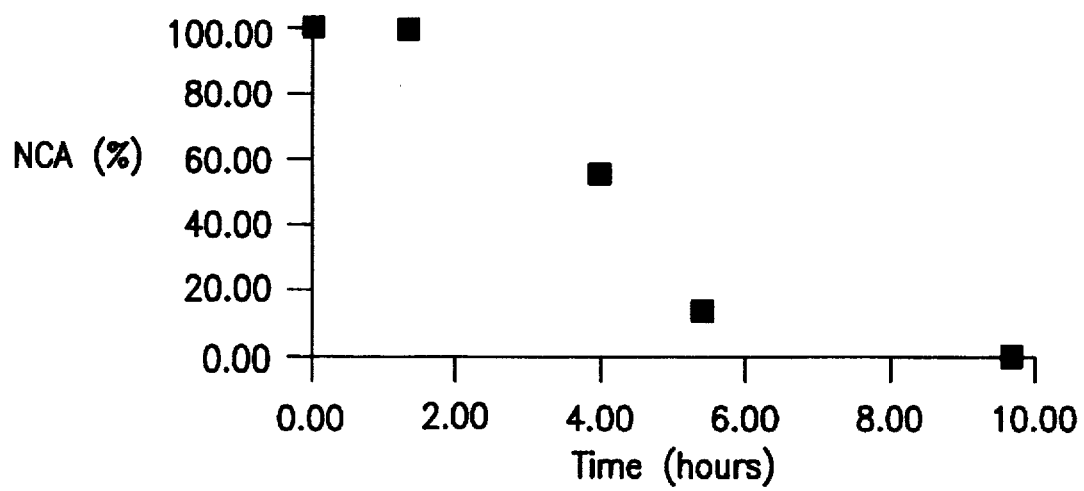
FIG. 4 represents the kinetic profile for disappearance of the NCAs, monitored by infrared, in the polymerization according to Example 4.

EXAMPLE 3: INFLUENCE OF THE INITIATOR 3.1 Polymerization of the Leu-NCA/Glu(OMe)-NCA Mixture with Water Example 2 was repeated, leaving out the triethylamine and adding an amount of water equal to 10% by weight of the dioxane. The kinetic profile of disappearance of the NCAs, monitored by infrared, indicates that the polymerization is complete in 8 h (cf. FIG. 4 attached). The reaction medium is then treated in the same way as in the case of a standard polymerization. A white solid is recovered (weight yield=97%), the $^1$H NMR spectrum of which is identical to that of a Leu-Glu(OMe) copolymer. The reduced viscosity of this product in trifluoroacetic acid is very low: $\eta_{red}$=0.48 dl/g. This comparative test shows that water, used alone without initiator, leads to the formation of a copolymer of low molar mass.

EXAMPLE 4: CORRESPONDENCE BETWEEN WEIGHT-AVERAGE MOLAR MASS M$_w$ AND REDUCED VISCOSITY $\eta_{red}$ Three samples (1 to 3) of different leucine/methyl glutamate copolymers (Leu/Glu(OMe)≃47/53 molar) were prepared according to the procedure of Example 2. Their weight-average molar masses M$_w$ were determined by light diffusion. Their reduced viscosities were, themselves, measured as indicated above. The results in Table 4 below clearly show that M$_w$ and $\eta_{red}$ vary in the same direction. There is thus a direct correlation between these two magnitudes.

TABLE 4

| SAMPLES | M$_w$ | $\eta_{red}$ |
|---|---|---|
| 1 | 325,000 | 1.8 |
| 2 | 290,000 | 1.6 |
| 3 | 100,000 | 1.1 |

We claim:

1. A method for the preparation of polyamino acids, with controlled molecular weights, by polymerization of N-carboxyanhydrides (NCAs) of at least one amino acid, using at least one alkaline initiator in liquid medium,
    wherein the improvement comprises using an initiator chosen from tertiary phosphines and/or amines;
    introducing into the polymerization medium:
        an amount of water of between 0.1 and 50% by weight relative to the rest of the liquid medium,
        and/or an amount of alcohol of less than or equal to 3000 mol % relative to the NCAs; and
    varying the amount of water and/or alcohol introduced in the polymerization medium, in order to control the molecular weight of the final polymers.

2. A method according to claim 1 wherein the amount of water relative to the rest of the liquid medium is between 0.5 and 10% by weight.

3. A method according to claim 1 wherein the amount of water relative to the rest of the liquid medium is between 1 and 5% by weight.

4. A method according to claim 1 wherein the amount of alcohol relative to the NCAs is from 10 to 1000 mol %.

5. A method according to claim 1 wherein the amount of alcohol relative to the NCAs is from 10 to 500 mol %.

6. A method according to claim 2 wherein the amount of alcohol relative to the NCAs is from 10 to 1000 mol %.

7. A method according to claim 3 wherein the amount of alcohol relative to the NCAs is from 10 to 500 mol %.

8. A method according to claim 1, which comprises the further steps of:
    establishing, for one or more given polyamino acids, a curve showing reduced viscosity of the polymers obtained as a function of the concentration of water and/or of alcohol in the liquid reaction medium,
    selecting a certain reduced viscosity for a target polyamino acid,
    determining, using the curve, the corresponding amount of water and/or alcohol,
    and carrying out the polymerization with this amount, so as to obtain the target polyamino acid.

9. A method according to claim 1, wherein the alcohol is a linear or cyclic $C_{1-24}$ monoalcohol, dialcohol, a mixture thereof, or an aromatic alcohol.

10. A method according to claim 9, wherein the alcohol is selected from the group consisting of methanol, ethanol, propanol, butanol, hexanol, phenols, glycols, and mixtures thereof.

11. A method according to claim 1, whereint the liquid medium comprises an organic cosolvent.

12. A method according to claim 1, wherein the NCAs are obtained from at least one amino acid selected from the group consisting of glycine, alanine, phenylalanine, leucine, isoleucine, valine, α-aminoisobutylic acid, pentamethylenespiroaminoacetic acid, aspartic acid, glutamic acid, α-aminoadipic acid, ornithine, lysine, arginine, cysteine, methionine, threonine, serine, and tyrosine.

13. A method according to claim 11, wherein the organic cosolvent is selected from the group consisting of:

cyclic or linear ethers, nitriles, halogenated aliphatics, aromatics, halogenated aromatics, nitro derivatives, esters, ketones, amides, sulfones, sulfoxides, and mixtures thereof.

14. A method according to claim 13, wherein the organic cosolvent is selected from the group consisting of dioxane, tetrahydrofuran, acetonitrile, chloroform, dichloromethane, 1,2-dichloroethane, toluene, xylene, nitromethane, methyl acetate, DMF, and DMSO.

15. A method according to claim 14, wherein the organic cosolvent is dioxane.

16. A method for controlling the molecular weight of polyamino acids prepared by polymerization of N-carboxyanhydrides (NCAs) of at least one amino acid, using at least one initiator selected from the group consisting of tertiary phosphines, tertiary amines and mixtures thereof, and in a liquid medium, to which is optionally added at least one organic cosolvent, said method consisting in using water and/or alcohol which is introduced into the polymerization medium in specific amounts.

* * * * *